United States Patent
Sjoquist et al.

(10) Patent No.: US 12,121,737 B2
(45) Date of Patent: *Oct. 22, 2024

(54) WEARABLE CARDIOVERTER DEFIBRILLATOR SYSTEM WITH REMOTE ALERTS BASED ON PROXIMITY

(71) Applicant: WEST AFFUM HOLDINGS DAC, Dublin (IE)

(72) Inventors: Steven E. Sjoquist, Lynnwood, WA (US); David P. Finch, Bothell, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 237 days.

This patent is subject to a terminal disclaimer.

(21) Appl. No.: 17/483,609

(22) Filed: Sep. 23, 2021

(65) Prior Publication Data

US 2022/0088401 A1 Mar. 24, 2022

Related U.S. Application Data

(60) Provisional application No. 63/081,963, filed on Sep. 23, 2020.

(51) Int. Cl.
*A61N 1/00* (2006.01)
*A61N 1/04* (2006.01)
*A61N 1/39* (2006.01)
*H04W 4/02* (2018.01)
*H04W 76/14* (2018.01)

(52) U.S. Cl.
CPC ............ *A61N 1/3925* (2013.01); *A61N 1/046* (2013.01); *A61N 1/0484* (2013.01); *A61N 1/3904* (2017.08); *H04W 4/023* (2013.01); *H04W 76/14* (2018.02)

(58) Field of Classification Search
None
See application file for complete search history.

(56) References Cited

U.S. PATENT DOCUMENTS

| 3,724,355 A | 4/1973 | Busch et al. |
| 4,583,524 A | 4/1986 | Hutchins |
| 4,619,265 A | 10/1986 | Morgan et al. |

(Continued)

FOREIGN PATENT DOCUMENTS

| CN | 101184525 A | 5/2008 |
| CN | 101631589 A | 1/2010 |

(Continued)

OTHER PUBLICATIONS

Heartstart MRx and XL AED Algorithm—Application Note, Jul. 2001, Edition 2 Philips Healthcare, USA.

(Continued)

*Primary Examiner* — John R Downey
*Assistant Examiner* — Anant A Gupta
(74) *Attorney, Agent, or Firm* — Polsinelli PC

(57) ABSTRACT

A WCD system is configured to monitor various characteristics of the WCD system including about the patient. The WCD system is further configured to transmit a notification of a notifiable event to responders that are outside a local area of the patient, and to silence the notification for any responder(s) that are inside the local area of the patient.

20 Claims, 7 Drawing Sheets

(56) References Cited

U.S. PATENT DOCUMENTS

| | | | |
|---|---|---|---|
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,120,488 B2 | 10/2006 | Nova |
| 7,463,922 B1 | 12/2008 | Snyder |
| 7,559,902 B2 | 7/2009 | Ting et al. |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,024,037 B2 | 9/2011 | Kumar |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,838,235 B2 | 9/2014 | Cowan |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,047,648 B1 | 6/2015 | Lekutai et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,339,663 B2 | 5/2016 | Sullivan et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 11,235,143 B2 * | 2/2022 | Medema ............ A61N 1/3925 |
| 2002/0133197 A1 | 9/2002 | Snyder |
| 2002/0181680 A1 | 12/2002 | Linder et al. |
| 2003/0158593 A1 | 8/2003 | Heilman et al. |
| 2004/0249418 A1 | 12/2004 | Mills |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Vollpe et al. |
| 2009/0005827 A1 | 1/2009 | Weintraub et al. |
| 2009/0171166 A1 * | 7/2009 | Amundson ............ A61B 5/1113 |
| | | 600/301 |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0197324 A1 | 8/2012 | Nova |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0282072 A1 | 10/2013 | Abdeen |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0043149 A1 | 2/2014 | Cowan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039040 A1 | 2/2015 | Cowan |
| 2015/0039053 A1 | 2/2015 | Kaib et al. |
| 2015/0112704 A1 * | 4/2015 | Braun .................... G06Q 10/10 |
| | | 705/2 |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2015/0352367 A1 | 12/2015 | Quan |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0148495 A1 | 5/2016 | Buchanan |
| 2016/0256104 A1 | 9/2016 | Romem et al. |
| 2016/0283900 A1 | 9/2016 | Johnson et al. |

(56) References Cited

U.S. PATENT DOCUMENTS

| | | | |
|---|---|---|---|
| 2017/0014073 A1 | 1/2017 | Shoshani et al. | |
| 2017/0027469 A1 | 2/2017 | Amir et al. | |
| 2017/0036066 A1 | 2/2017 | Chahine | |
| 2017/0040758 A1 | 2/2017 | Amir et al. | |
| 2017/0056682 A1 | 3/2017 | Kumar et al. | |
| 2017/0162840 A1 | 6/2017 | Pendry | |
| 2017/0281060 A1* | 10/2017 | Wedekind | G16H 10/40 |
| 2017/0319862 A1 | 11/2017 | Foshee, Jr. et al. | |
| 2017/0367591 A1 | 12/2017 | Jorgensen | |
| 2018/0055442 A1 | 3/2018 | Freeman | |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0221645 A1* | 8/2018 | Medema | A61N 1/0484 |
| 2018/0243578 A1 | 8/2018 | Volosin | |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0321650 A1 | 10/2019 | Raymond et al. | |
| 2020/0090485 A1* | 3/2020 | Casse | G16H 20/40 |

FOREIGN PATENT DOCUMENTS

| | | |
|---|---|---|
| CN | 102573990 A | 7/2012 |
| CN | 103354756 A | 10/2013 |
| DE | 2005060985 A2 | 6/2007 |
| EP | 2305110 A1 | 4/2011 |
| EP | 3357534 B1 | 2/2020 |
| JP | 4320257 A | 3/2005 |
| JP | 2005319306 A | 11/2005 |
| JP | 2013511222 A | 3/2013 |
| JP | 5963767 A | 1/2014 |
| JP | 2014526282 A | 10/2014 |
| JP | 2016209603 A | 12/2016 |
| WO | 98/39061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |
| WO | 2016154425 A1 | 9/2016 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

First Office Action mailed Mar. 30, 2021, issued in Chinese Patent Application No. 201810085761.X, filed Jan. 29, 2018, 18 pages.

Japanese Office Action mailed Dec. 18, 2018, issued in Japanese Application No. 2018-016636, filed Oct. 3, 2017, 5 pages.

European Search Report mailed Feb. 23, 2018, issued in EP Application No. 17194049.7-1124, filed Sep. 29, 2017, 10 pages.

European Search Report mailed Mar. 9, 2013, issued in EP Application No. 18152890.2-1124, filed Jan. 23, 2018, 7 pages.

\* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

Sample Components of a WCD System
With Proximity-Based Notifications

*General Communication Arrangement*

WEARABLE CARDIOVERTER DEFIBRILLATOR SYSTEM WITH REMOTE ALERTS BASED ON PROXIMITY

CROSS REFERENCE TO RELATED PATENT APPLICATIONS

This patent application claims priority from U.S. Provisional Patent Application No. 63/081,963, filed on Sep. 23, 2020, entitled "WCD System With Remote Alerts Based on Proximity," the disclosure of which is hereby incorporated by reference for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include individuals who have had a heart attack, or a prior SCA episode. A frequent recommendation is for these people to receive an Implantable Cardioverter Defibrillator ("ICD"). The ICD is surgically implanted in the chest, and continuously monitors the person's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardioverter defibrillator ("WCD") system. A WCD system typically includes a harness, vest, or other garment for wearing by the patient. The system includes a defibrillator and external electrodes, which are attached on the inside of the harness, vest, or other garment. When a patient wears a WCD system, the external electrodes may then make good electrical contact with the patient's skin, and therefore can help monitor the patient's ECG. If a shockable heart arrhythmia is detected, then the defibrillator of the WCD system delivers the appropriate electric shock through the patient's body, and thus through the heart.

BRIEF SUMMARY

In accordance with aspects of this disclosure, a WCD system is configured to detect whether to send notifications to remote responders of an event. In some embodiments, the WCD system is configured to make a determination to send such notifications only to responders that are outside of a local area around the WCD system. In other embodiments, the WCD system is configured to send such notifications to any receiving responders, and each receiving responder is configured to either announce the notification or silence the notification depending on whether the receiving responder is inside or outside the local area of the WCD system.

In some embodiments, the WCD system transmits the notifications as SMS message to cell phone or smartphones of the responders. In other embodiments, the WCD system may make telephone calls to the responders in which the notifications may be in the form of recorded or synthesized voice messages. In yet other embodiments, the WCD system may send information to a WCD system server, which in turn sends SMS and/or voice messages to the responders, or emails or application notifications that the responders receive via email or notification apps running on their computers, smartphones, laptops or other "connected" devices.

In various embodiments, the WCD system transmits the information as an electronic message (e.g., SMS or MMS message, RCS message, email message, instant message, or the like) to a mobile device (e.g., mobile phone or tablet) of the responders. In other embodiments, the WCD system may make telephone calls to the responders in which the notifications may be in the form of recorded or synthesized voice messages. In yet other embodiments, the WCD system may send information to a WCD system server, which in turn sends messages to the responders, or email messages, or application notifications that the responders receive via email or notification apps running on their computers, smartphones, laptops or other "connected" devices.

The foregoing brief summary is illustrative only and is not intended to be in any way limiting. In addition to the illustrative aspects, embodiments, and features described above, which need not all be present in all embodiments of the inventions disclosed herein, further aspects, embodiments, and features are set forth in the drawings and the following detailed description.

DETAILED DESCRIPTION

A wearable cardioverter defibrillator (WCD) system made according to embodiments has several components. These components can be provided separately as modules that can be interconnected, or can be combined with other components, etc.

Figure 1:
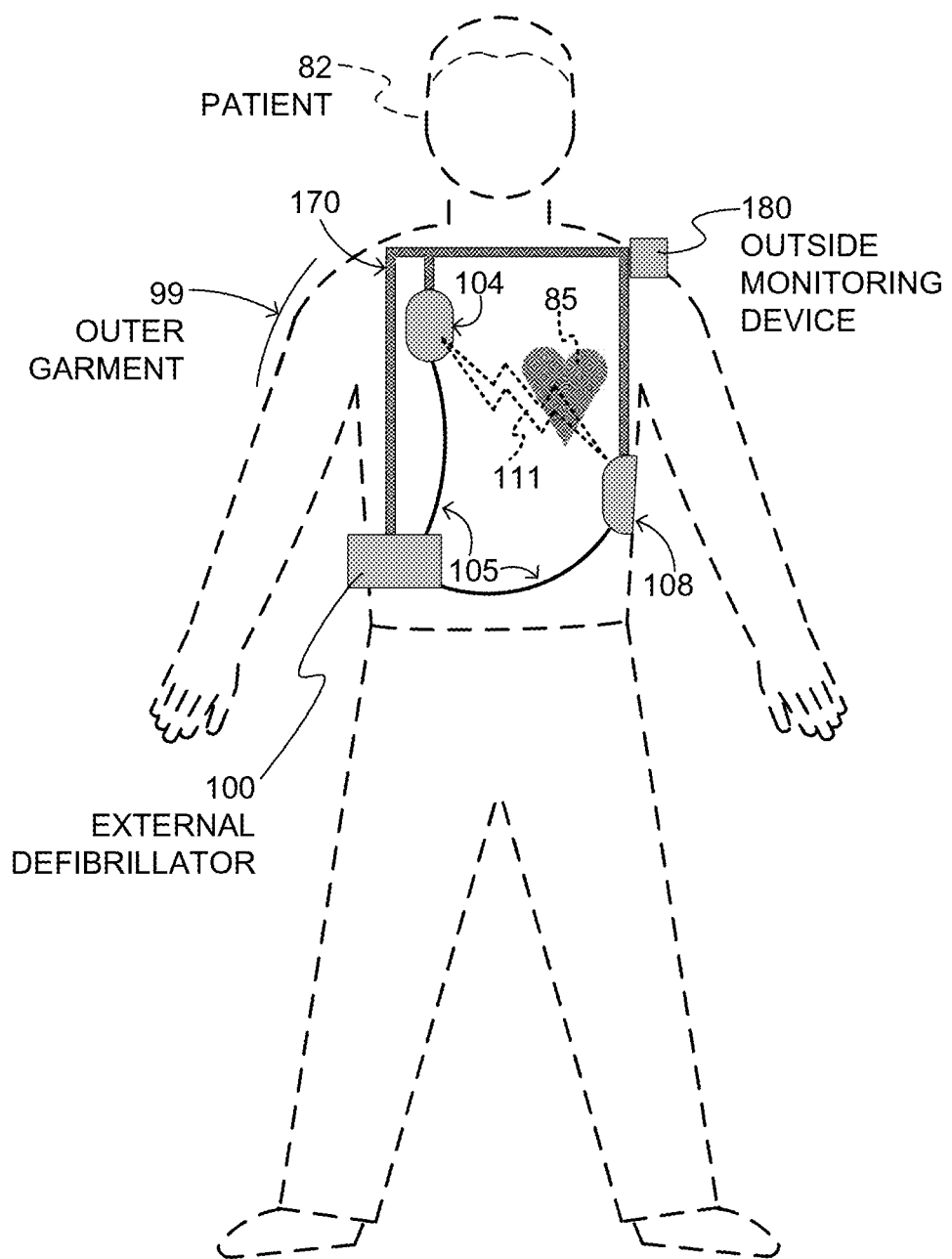
FIG. 1 is a diagram of components of a sample wearable cardioverter defibrillator (WCD) system, made according to embodiments.

FIG. 1 depicts a patient 102. Patient 102 may also be referred to as a person and/or wearer, since that patient wears components of the WCD system.

FIG. 1 also depicts components of a WCD system made according to embodiments. One such component is a support structure 118 that is wearable by patient 102. It will be understood that support structure 118 is shown only generically in FIG. 1, and in fact partly conceptually. FIG. 1 is provided merely to illustrate concepts about support structure 118, and is not to be construed as limiting how support structure 118 is implemented, or how it is worn.

Support structure 118 can be implemented in many different ways in different embodiments. For example, in one embodiment implemented in a single component or a combination of multiple components. In embodiments, support structure 118 could include a vest, a half-vest, a garment, etc. In such embodiments such items can be worn similarly to parallel articles of clothing. In embodiments, support structure 118 could include a harness, one or more belts or straps, etc. In such embodiments, such items can be worn by the patient around the torso, hips, over the shoulder, etc. In embodiments, support structure 118 can include a container or housing, which can even be waterproof. In such embodiments, the support structure can be worn by being attached to the patient by adhesive material, for example as shown in U.S. Pat. No. 8,024,037. Support structure 118 can even be implemented as described for the support structure of US Pat. App. No. US 2017/0056682 A1, which is incorporated herein by reference. After review of this disclosure, in such embodiments, the person skilled in the art will recognize that additional components of the WCD system can be in the housing of a support structure instead of attached externally to the support structure, for example as described in the 2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 108, and sample defibrillation electrodes 110, 112, which are coupled to external defibrillator 108 via electrode leads 114. Defibrillator 108 and defibrillation electrodes 110, 112 can be coupled to support structure 118. As such, many of the components of defibrillator 108 could be therefore coupled to support structure 118. When defibrillation electrodes 110, 112 make good electrical contact with the body of patient 102, defibrillator 108 can administer, via electrodes 110, 112, a brief, strong electric pulse 116 through the body. Pulse 116, also known as shock, defibrillation shock, therapy, or therapy shock, is intended to go through and restart heart 104, in an effort to save the life of patient 102. Pulse 116 can further include one or more pacing pulses, and so on.

A defibrillator typically decides whether to defibrillate based on an ECG signal of the patient. However, some embodiments of external defibrillator 108 can initiate defibrillation (or hold-off defibrillation) based on a variety of inputs, with ECG merely being one of them.

Accordingly, in some embodiments of external defibrillator 108, signals such as physiological signals containing physiological data are obtained from patient 102. While the patient may be considered a "user" of the WCD system, in some embodiments, for example, a user of the WCD may also be a clinician such as a doctor, nurse, emergency medical technician (EMT) or other similarly situated individual (or group of individuals). The particular context of these and other related terms within this description should be interpreted accordingly.

The WCD system may optionally include an outside monitoring device 120. Monitoring device 120 is called an "outside" device because it could be provided as a stand-alone device, for example not within the housing of defibrillator 108. Monitoring device 120 can be configured to sense or monitor at least one local parameter. A local parameter can be a parameter of patient 102, or a parameter of the WCD system, or a parameter of the environment, as will be described later in this document. Monitoring device 120 may include one or more transducers or sensors that are configured to render one or more physiological inputs from one or more patient parameters that it senses.

Optionally, device 120 is physically coupled to support structure 118. In addition, device 120 can be communicatively coupled with other components, which are coupled to support structure 118. Such communication can be implemented by a communication module, as will be deemed applicable by a person skilled in the art in view of this description.

Figure 2:
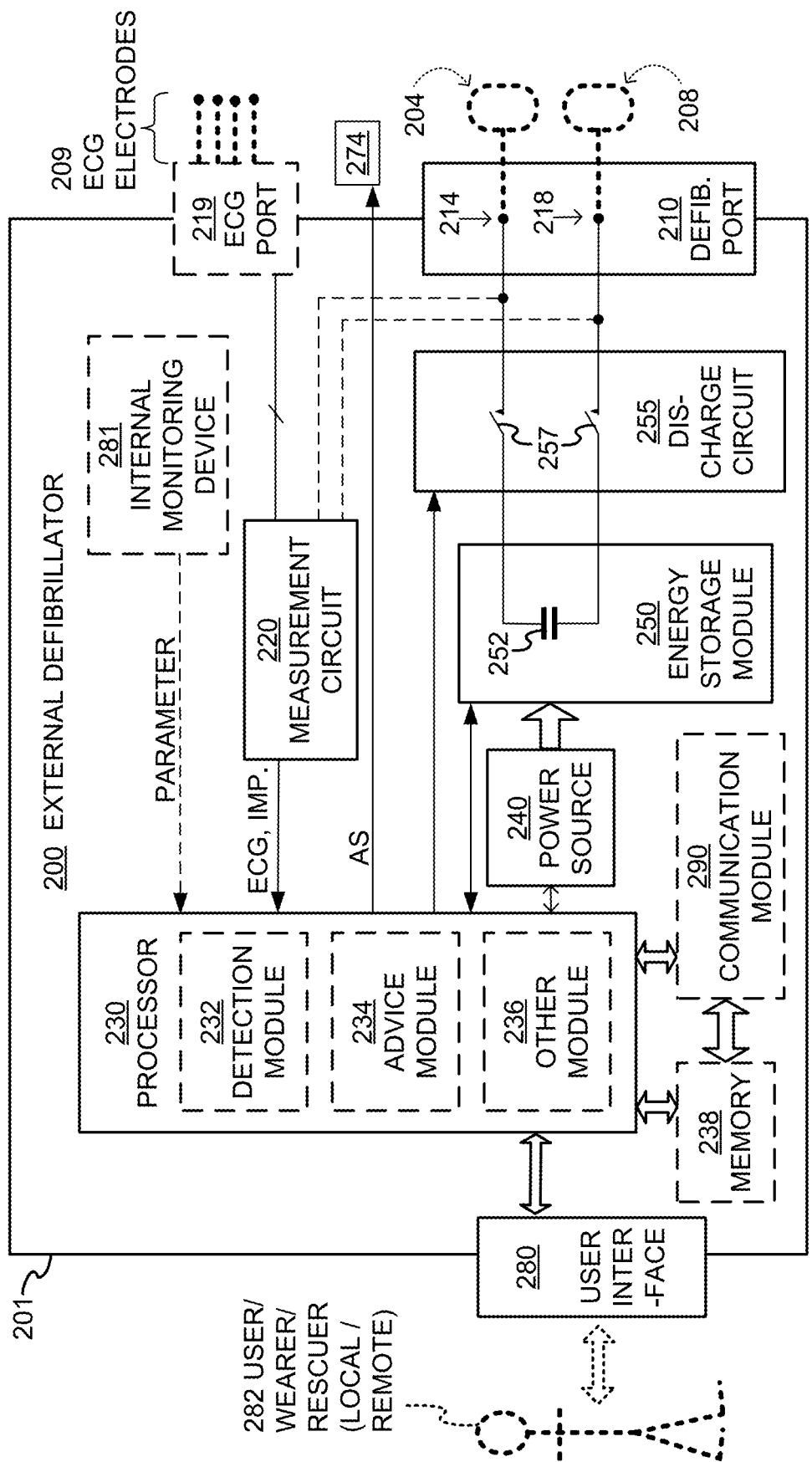
FIG. 2 is a diagram showing sample components of an external defibrillator, such as the one belonging in the WCD system of FIG. 1, and which is made according to embodiments.

FIG. 2 is a diagram showing components of an external defibrillator 202, made according to embodiments. These components can be, for example, included in external defibrillator 108 of FIG. 1. The components shown in FIG. 2 can be provided in a housing 204, which may also be referred to as casing 204.

External defibrillator 202 is intended for a patient who would be wearing it, such as patient 102 of FIG. 1. Defibrillator 202 may further include a user interface 244 for a user 248. User 248 can be patient 102, also known as wearer. Or user 248 can be a local rescuer at the scene, such as a bystander who might offer assistance, or a trained person. Or, user 248 might be a remotely located trained caregiver in communication with the WCD system.

User interface 244 can be made in many ways according to various embodiments. User interface 244 may include output devices, which can be visual, audible or tactile, for communicating to a user by outputting images, sounds or vibrations. Images, sounds, vibrations, and anything that can be perceived by user 248 can also be called human perceptible indications. There are many examples of output devices. For example, an output device can be a light, or a screen to display what is sensed, detected and/or measured, and provide visual feedback to rescuer 248 for their resuscitation attempts, and so on. Another output device can be a speaker, which can be configured to issue voice prompts, beeps, loud alarm sounds to warn bystanders, etc.

User interface 244 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 202 may include an internal monitoring device 246. Device 246 is called an "internal" device because it is incorporated within housing 204. Monitoring device 246 can sense or monitor patient parameters such as patient physiological parameters, system parameters and/or environmental parameters, all of which can be called patient data. In other words, internal monitoring device 246 can be complementary or an alternative to outside monitoring device 120 of FIG. 1. Allocating which of the parameters are to be monitored by which monitoring device can be done according to design considerations. Device 246 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 246 may include one or more sensors configured to acquire patient physiological signals. Examples of such sensors or transducers include electrodes to detect ECG data, a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an SpO2 sensor, and so on. It will be appreciated that such sensors can help detect the patient's pulse, and can therefore also be called pulse detection sensors, pulse sensors, and pulse rate sensors. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 102. A trend can be detected by comparing values of parameters at different times. Parameters whose detected trends can particularly help a cardiac rehabilitation program include: (a) cardiac function (e.g. ejection fraction, stroke volume, cardiac output, etc.); (b) heart rate variability at rest or during exercise; (c) heart rate profile during exercise and measurement of activity vigor, such as from the profile of an accelerometer signal and informed from adaptive rate pacemaker technology; (d) heart rate trending; (e) perfusion, such as from SpO2 or CO2; (f) respiratory function, respiratory rate, etc.; (g) motion, level of activity; and so on. Once a trend is detected, it can be stored and/or reported via a communication link, along perhaps with a warning. From the report, a physician monitoring the progress of patient 102 will know about a condition that is either not improving or deteriorating.

Patient state parameters include recorded aspects of patient 102, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 120 or monitoring device 246. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, one of the transducers may include a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed if monitoring device 120 or 246 includes a GPS location sensor as per the above.

Defibrillator 202 typically includes a defibrillation port 212, such as a socket in housing 204. Defibrillation port 212 includes electrical nodes 214, 216. Leads of defibrillation electrodes 206, 208, such as leads 114 of FIG. 1, can be plugged into defibrillation port 212, so as to make electrical contact with nodes 214, 216, respectively. It is also possible that defibrillation electrodes 206, 208 are connected continuously to defibrillation port 212, instead. Either way, defibrillation port 212 can be used for guiding, via electrodes, to the wearer the electrical charge that has been stored in an energy storage module 234 that is described more fully later in this document. The electric charge will be the shock for defibrillation, pacing, and so on.

Defibrillator 202 may optionally also have an ECG port 218 in housing 204, for plugging in sensing electrodes 210, which are also known as ECG electrodes and ECG leads. It is also possible that sensing electrodes 210 can be connected continuously to ECG port 218, instead. Sensing electrodes 210 are types of transducers that can help sense an ECG signal, e.g. a 12-lead signal, or a signal from a different number of leads, especially if they make good electrical contact with the body of the patient. Sensing electrodes 210 can be attached to the inside of support structure 118 for making good electrical contact with the patient, similarly as defibrillation electrodes 206, 208.

Optionally, a WCD system according to embodiments also includes a fluid that it can deploy automatically between the electrodes and the patient's skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 206, 208, and sensing electrodes 210.

The fluid may be initially stored in a fluid reservoir, not shown in FIG. 2, which can be coupled to the support structure. In addition, a WCD system according to embodiments further includes a fluid deploying mechanism 242. Fluid deploying mechanism 242 can be configured to cause at least some of the fluid to be released from the reservoir, and be deployed near one or both of the patient locations, to which the electrodes are configured to be attached to the patient. In some embodiments, fluid deploying mechanism 242 is activated prior to the electrical discharge responsive to receiving activation signal AS from processor 222 that is described more fully later in this document.

In some embodiments, defibrillator 202 also includes a measurement circuit 220, as one or more of its sensors or transducers. Measurement circuit 220 senses one or more electrical physiological signals of the patient from ECG port 218, if provided. Even if defibrillator 202 lacks ECG port 218, measurement circuit 220 can obtain physiological signals through nodes 214, 216 instead, when defibrillation electrodes 206, 208 are attached to the patient. In these cases, the physiological input reflects an ECG measurement. The parameter can be an ECG, which can be sensed as a voltage difference between electrodes 206, 208. In addition, the parameter can be an impedance, which can be sensed between electrodes 206, 208 and/or the connections of ECG port 218. Sensing the impedance can be useful for detecting, among other things, whether these electrodes 206, 208 and/or sensing electrodes 210 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 202 also includes a processor 222. Processor 222 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 222 may include, or have access to, a non-transitory storage medium, such as Memory 230 that is described more fully later in this document. Such a memory can have a non-volatile component for storage of machine-readable and machine-executable instructions. A set of such instructions can also be called a program. The instructions, which may also be referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module implemented using software includes a set of the instructions so as to offer or fulfill a particular functionality. Embodiments of modules and the functionality delivered are not limited by the embodiments described in this document.

Processor 222 can be considered to have one or more modules. One such module can be a detection module 224. Detection module 224 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 224 can also include a Ventricular Tachycardia (VT) detector, and so on.

Another such module in processor 222 can be an advice module 226, which generates advice for what to do. The advice can be based on outputs of detection module 224. There can be many types of advice according to embodiments. In some embodiments, the advice is a shock/no shock determination that processor 222 can make, for example via advice module 226. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Various embodiments of processor 222 can include additional modules, such as other module 236, for other functions. In addition, if internal monitoring device 246 is indeed provided, it may be operated in part by processor 222, etc.

Embodiments of defibrillator 202 optionally further includes a Memory 230, which can work together with processor 222. Memory 230 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 230 is thus a non-transitory storage medium. Memory 230, if provided, can include programs for processor 222, which processor 222 may be able to read and execute. More particularly, the programs can include sets of instructions in the form of code, which processor 222 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 222, and can also include protocols and ways that decisions can be made by advice module 226. In addition, Memory 230 can store prompts for user 248, if this user is a local rescuer. Moreover, Memory 230 can store data. This data can include patient data, system data and environmental data, for example as learned by internal monitoring device 246 and outside monitoring device 120. The data can be stored in Memory 230 before it is transmitted out of defibrillator 202 or stored there after it is received by defibrillator 202.

Defibrillator 202 may also include a power source 232. To enable portability of defibrillator 202, power source 232 typically includes a battery. Such a battery is typically implemented as a battery pack, which can be rechargeable or not. Sometimes a combination is used of rechargeable and non-rechargeable battery packs. Other embodiments of power source 232 can include an AC power override, for where AC power will be available, an energy storage capacitor, and so on. In some embodiments, power source 232 is controlled by processor 222. Appropriate components may be included to provide for charging or replacing power source 232.

Defibrillator 202 may additionally include an energy storage module 234. Energy storage module 234 can be coupled to the support structure of the WCD system, for example either directly or via the electrodes and their leads. Module 234 is where some electrical energy can be stored temporarily in the form of an electrical charge, when preparing it for discharge to administer a shock. In embodiments, module 234 can be charged from power source 232 to the desired amount of energy, as controlled by processor 222. In typical implementations, module 234 includes a capacitor 236, which can be a single capacitor or a system of capacitors, and so on. In some embodiments, energy storage module 234 includes a device that exhibits high power density, such as an ultracapacitor. As described above, capacitor 236 can store the energy in the form of an electrical charge, for delivering to the patient.

Defibrillator 202 moreover includes a discharge circuit 238. When the decision is to shock, processor 222 can be configured to control discharge circuit 238 to discharge through the patient the electrical charge stored in energy storage module 234. When so controlled, discharge circuit 238 can permit the energy stored in energy storage module 234 to be discharged to nodes 214, 216, and from there also to defibrillation electrodes 206, 208, so as to cause a shock to be delivered to the patient. Circuit 238 can include one or more switches 240. Switches 240 can be made in a number of ways, such as by an H-bridge, and so on. Circuit 238 can also be controlled via user interface 244.

Defibrillator 202 can optionally include a communication module 250, for establishing one or more wired or wireless communication links with other devices of other entities, such as a remote assistance center, Emergency Medical Services (EMS), and so on. Module 250 may also include such sub-components as may be deemed necessary by a person skilled in the art, for example an antenna, portions of a processor, supporting electronics, outlet for a telephone or a network cable, etc. This way, data, commands, etc. can be communicated. The data can include patient data, event information, therapy attempted, CPR performance, system data, environmental data, and so on. Defibrillator 202 in some embodiments can optionally include other components.

Returning to FIG. 1, in embodiments, one or more of the components of the shown WCD system have been customized for patient 102. This customization may include a number of aspects. For instance, support structure 118 can be fitted to the body of patient 102. For another instance, baseline physiological parameters of patient 102 can be measured, such as the heart rate of patient 102 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

Figure 3:
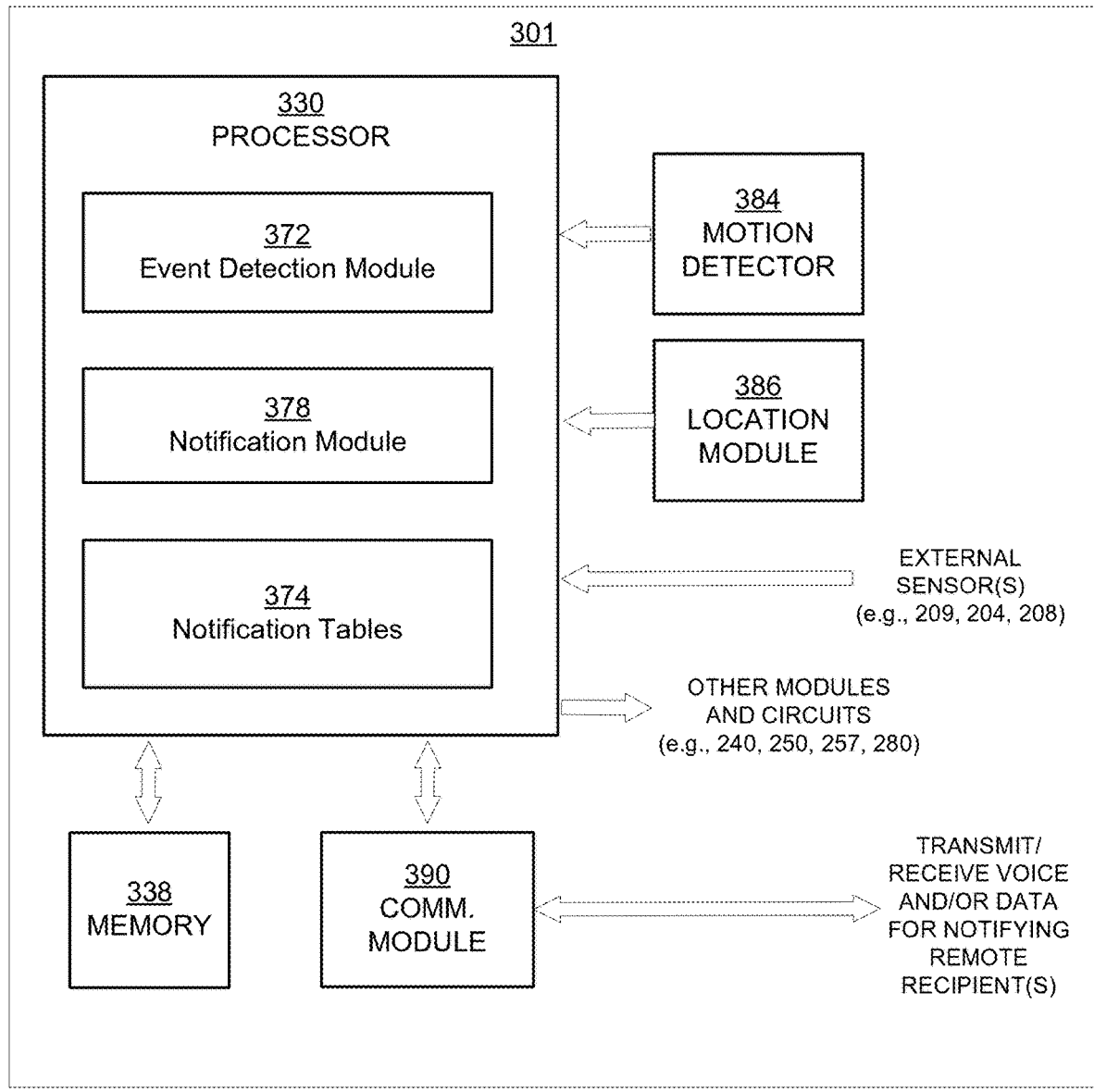
FIG. 3 is a diagram showing a collection of sample components of WCD systems for notifying remote responders, made according to embodiments.

FIG. 3 is a diagram showing sample components of an external defibrillator 301 similar to those of external defibrillator 202 of FIG. 2, in which some components are shown in more detail and some in less detail, according to embodiments. External defibrillator 301 can implemented in a WCD to deliver appropriate therapy (e.g., defibrillation shocks, cardioversion shocks, pacing, etc.) to a patient with an arrhythmia.

In embodiments, external defibrillator 301 includes a processor 330 coupled to a memory 338, a motion detector 384, a location module 386, and a communication module 390. Processor 330, memory 338, and communication module 390 are implemented in some embodiments as described above in conjunction with FIG. 2 for processor 222, Memory 230, and communication module 250. Memory 338 can also be configured with patient ID information intended for inclusion in notifications that are described further below. External defibrillator 301, in embodiments, may also include other modules and components as shown in FIG. 2, but are omitted in FIG. 3 for simplicity of discussion.

In some embodiments, the components of external defibrillator 301 shown in FIG. 3 are disposed in a single housing or unit that is coupled to the support structure such as support structure 118 (FIG. 1). In other embodiments, one or more of these components are distributed over other parts of the WCD system. For example, in some embodiments, processor 330, location module 386 and communication module 390 are implemented at least in part using a mobile personal communication device such as a smartphone-like device as described below in conjunction with FIG. 5.

Motion detector 384, in some embodiments, is configured to detect motion of the patient, including patient motion due to having CPR performed on the patient. In embodiments, motion detector 384 is implemented using one or more of an accelerometer, force sensor, position sensor, transthoracic impedance sensors, etc. Some examples of position sensors include UWB position sensors, and magnetic field position sensors such as used in TrueCPR™ devices available from Physio-Control, Inc., Redmond, WA.

Location module 386, in some embodiments, is configured to determine the location of the patient. In some embodiments location module 386 determines the location of external defibrillator 301, other component of the WCD system, or possibly an accessory associated with the WCD system, to indicate the approximate location of the patient. Location module 386 in some embodiments uses one or more of GPS, cellular tower location, Wi-Fi access point locations, inertial navigation, etc. to determine the location of the patient. In embodiments of the WCD system having a mobile communication device (e.g., smartphone-like device), the location module may be incorporated into the mobile communication device and include an API to interface with a location service, such as Google Location Services.

In addition, in some embodiments processor 330 includes an event detection module 372, a notification module 378, and one or more notification tables 374. In some embodiments event detection module 372 and notification module 378 are implemented at least in part using software or programming stored in memory 338.

Event detection module 372 is configured to monitor the various sensors, inputs, and other circuits of the WCD system to identify a "notifiable event." For the purpose of this discussion, the term "notifiable event" refers to an event pertaining to the WCD system or to the patient for which a notification should be transmitted to one or more responders. Many different occurrences may constitute a notifiable event. For example, the event detection module 372 may monitor the patient's physiological signals (via, e.g., measurement circuit 220) for the occurrence of a medical event (e.g., VT, VF, or other SCA), which would likely constitute a notifiable event. However, less urgent occurrences could also constitute notifiable events. For instance, system parameters may give rise to maintenance issues such as a low battery or other malfunction with the WCD system, which may give rise to notifiable events. In addition, notifiable events may be programmable by the patient or other person using the WCD, such as via user interface 244.

In accordance with this disclosure, different notifiable events may implicate different types of information. For example, the WCD system may experience only a minor maintenance issue, which could constitute a notifiable event since the proper operation of the WCD system is important to its effectiveness. In such an event, the patient's physiological data (e.g., ECG trace data) would be less relevant to the event. Alternatively, if the patient experiences a critical medical event (e.g., SCA), the WCD system maintenance data would likely be less relevant than the patient's physiological data. Accordingly, and as discussed in greater detail below, different notifiable events may have different patient information associated therewith.

Notification module 378 is configured to determine whether one or more other people or parties (also referred to as responders in this context) should be notified, such as when event detection module 372 identifies that a notifiable event has occurred. In some embodiments, notification module 378 is configured to determine whether one or more other people or parties should be notified that the patient or the WCD has experienced some notifiable event.

In some embodiments, different responders or, perhaps, classes of responders may be dissimilarly situated regarding what information should be transmitted to such responders. For example, a medical professional, such as the patient's doctor, could understand and make use of significantly more information about the patient's physiological data (e.g., the patient's ECG trace, blood oxygen levels, etc.) than could the patient's family members. Indeed, much of the information monitored by the WCD system would likely be unusable and even confusing to the typical lay person. Similarly, certain Emergency Medical Services (EMS) personnel would likely be most interested in certain patient information (e.g., the patient's vital signs and location) while other information may be less relevant (e.g., maintenance information about the WCD system). Likewise, responders that are in close proximity to the patient may be either in greater or lesser need of certain information about the patient than responders who are not in close proximity to the patient. In such cases, different sets of information may be appropriate for presentation to responders based on the proximity of the responders to the patient.

Accordingly, the notification module 378 may be configured to transmit different notifications to different responders based on the proximity of the responder to the WCD system 301. For the purpose of this discussion, the term "patient information" refers to any data collected or detected by the WCD system about the patient or about the WCD system itself. Patient information may include, but is not limited to, patient state parameters, patient physiological data, system parameters, environmental parameters, and WCD maintenance data. Patient information may further include patient location information. In addition, patient information may include data about any medical events that the patient may be experiencing or may have experienced. Still further, patient information may include data about any therapy provided to or other actions performed on the patient. Other examples of patient information will become clear to those skilled in the art from a study of this disclosure.

Notification module 378, in some embodiments, is configured to obtain event information, patient identification information, patient location information, and recipient contact information in response to a determination that one or more responders should be notified. In some embodiments, the event information (for example, Shock Delivered, VF Detected, VT Detected, Bradycardia Detected and/or Asystole Detected) and the patient identification information is obtained from memory 338 and/or one or more modules of processor 330 such as, for example, modules 232, 234, and 236 (previously described in conjunction with FIG. 2). Notification module 378 in some embodiments is configured to obtain patient location information from location module 386. In some embodiments, the recipient contact information can be entered by the user or clinician when the patient is fitted with the WCD system and updated as desired. The responders can be people who might be expected to be near patient 182 for significant periods of time such as, for example, spouse, relatives, neighbors, co-workers, assistants, etc. so that assistance can be quickly provided to patient 182.

In a further refinement, after a notification is sent in response to the occurrence of a notifiable event, notification module 378 may be configured to cause the notification to be periodically resent (e.g., every 60 seconds). In some embodiments, the resending of notifications may be terminated in response to one or more responders sending a message to the WCD system (or, perhaps, an affiliated accessory) that the responder(s) are in the process of responding to the notification. Alternatively, the notification itself could include a component (e.g., a read receipt, beacon, tracking pixel, or the like) to automatically return an indication that the notification has been received and, perhaps, read.

In some embodiments, WCD system 301 includes a proximity detector (not shown) such as, for example, disclosed in U.S. Pat. No. 9,339,663 issued May 17, 2016, and entitled "WEARABLE CARDIAC DEFIBRILLATOR SYSTEM EMITTING CPR PROMPTS", incorporated by reference herein in its entirety. The proximity detector can be used to detect when bystanders are near the patient. Responsive to the proximity detector detecting such a bystander, in some embodiments, notification module 378 is configured to make a determination that a notification need not be sent to potential responders. Conversely, responsive to the proximity detector detecting that there are no nearby bystanders, in some embodiments notification module 378 will make a determination that a notification should be sent to responders.

In still other embodiments, when the aforementioned proximity detector detects nearby bystanders, notification module 378 may be configured to make a determination that a notification should not be sent to responders. However, in addition, if after a preset period of time (e.g., 30 seconds) the WCD system does not detect CPR has been started on the patient, notification module 378 may be further configured to change the determination so that a notification should be sent to the responders. In some embodiments, the WCD system may detect CPR by detecting changes in the patient's transthoracic impedance.

Communication module 390, in some embodiments, is configured to transmit at least some of the information obtained by the notification module to one or more respondents using the recipient contact information. In some embodiments, communication module 390 is implemented using a wireless transceiver such as, for example, cellular voice, cellular data, SMS, Wi-Fi, "Wi-Fi Direct", Bluetooth, ZigBee, Near Field Communication ("NFC"), etc. In some embodiments, these wireless connections may be used to communicate via a server that is configured to initiate communications to the one or more responders using SMS, email, voice (cellular and POTS), client application notifications (e.g., client apps configured on respondents' computing devices such as smartphones), etc. to the one or more responders. Various embodiments of these communications are described below.

The above-described embodiments of a WCD system can be advantageously used to provide notifications to various remote responders based, at least in part, on the particular responders' proximity to the patient. For example, if a responder is already in the immediate vicinity of the patient, that responder would not necessarily need to receive a notification that included the patient's location. Indeed, responder(s) who are already in close proximity to the patient may be fully engaged in attending aid to the patient. In such a case, notifications with unnecessary information could distract such responder(s) and potentially compromise the patient's aid. Conversely, if a responder were not in the immediate vicinity of the patient, that responder may be in need of a notification that included information indicating the patient's location so that the responder(s) can go as quickly as possible to the patient and provide additional assistance such as CPR.

Figure 4:
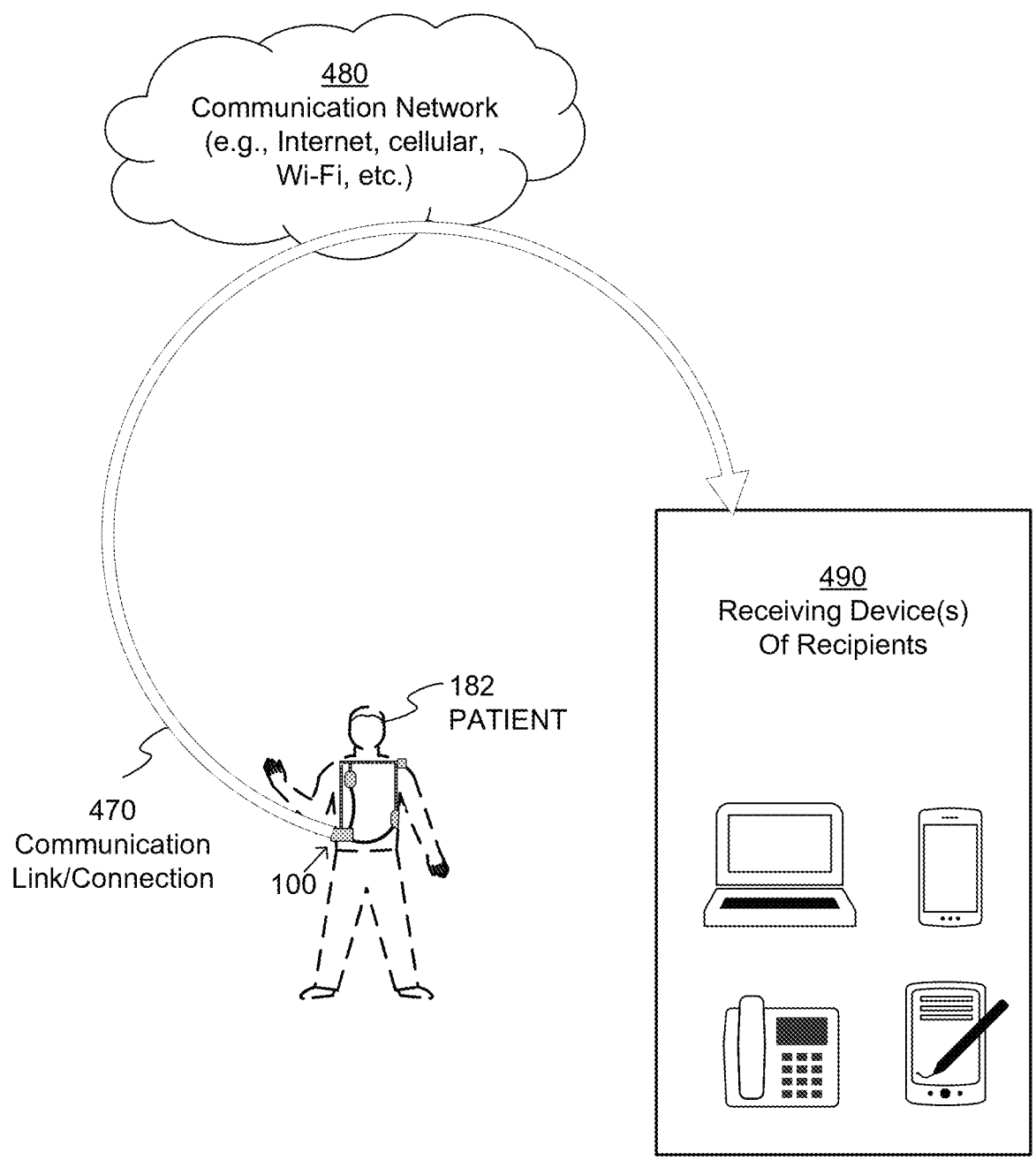
FIG. 4 is a diagram showing a general communication arrangement for a WCD system for issuing notifications to various interested groups by profile, made according to embodiments.

FIG. 4 is a conceptual diagram showing a general communication arrangement for a WCD system for notifying remote responders, made according to embodiments. FIG. 4 illustrates a general flow of a notification of some notifiable event from the WCD system (e.g., from patient worn external defibrillator 108 as described in conjunction with FIG. 1), over a communication link/connection 470 to each of one or more remote responders via a communication network 480. Each remote responder may receive a respective notification using the remote responders' receiving devices 490. Communication network 480 is implemented according to various embodiments using a combination of wireless and/or wired sub links that can include Bluetooth connections, wireless LAN networks (e.g., Wi-Fi networks), the Internet, POTS, cellular voice networks, cellular data networks, and/or other communication networks. The respondents' devices 490 can include, according to embodiments, computers connected to the communication network 480, cellular telephones, landline telephones, pagers, PDAs, tablet computing devices, and/or smartphones configured with notification applications, etc.

Figure 5:
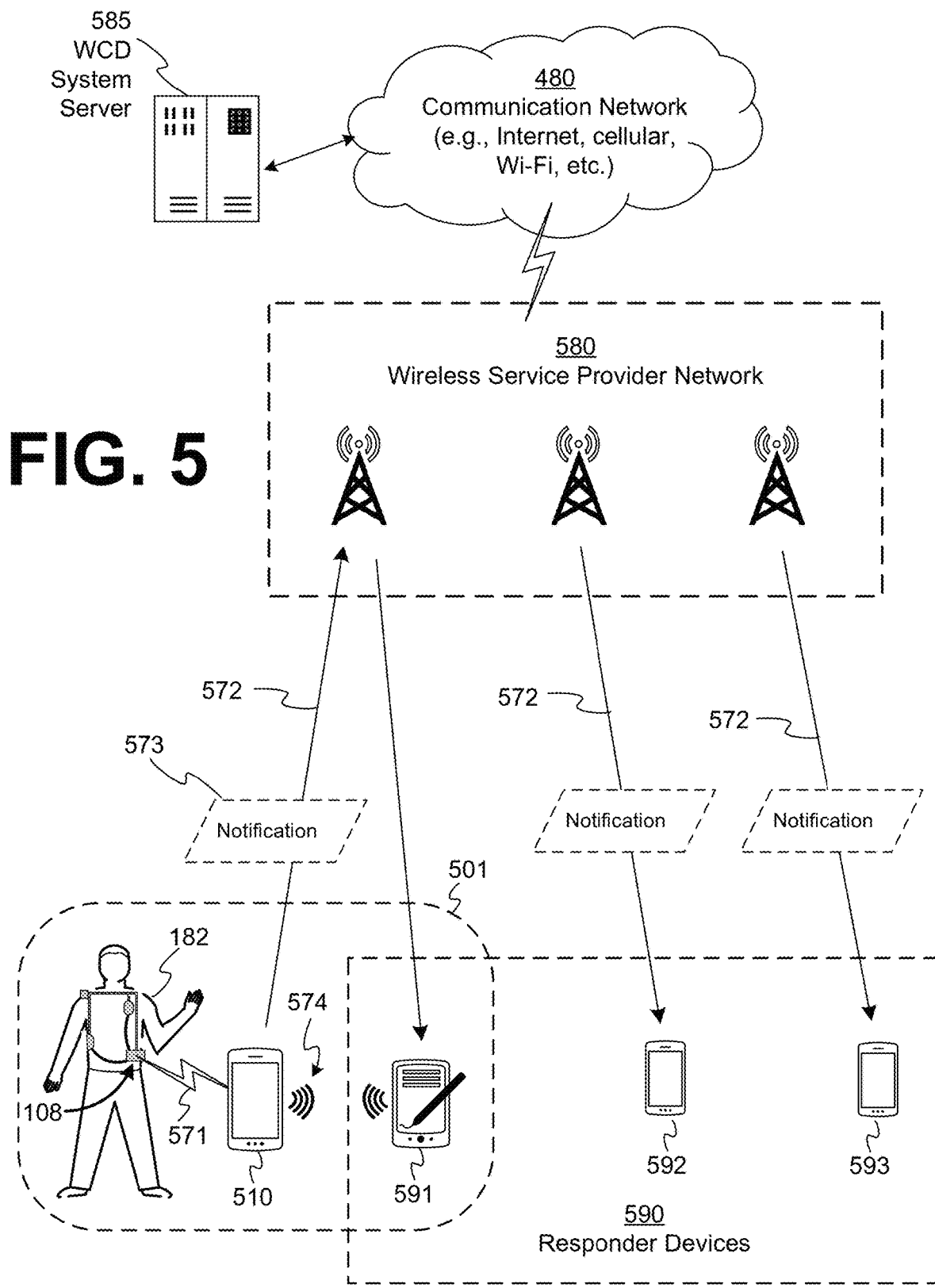
FIG. 5 is a diagram showing a communication arrangement for a WCD system having a mobile communication device for notifying remote responders, made according to embodiments.

FIG. 5 is a diagram showing an embodiment of a particular communication arrangement implementing the general arrangement shown in FIG. 4. The arrangement of FIG. 5, in this embodiment, includes a mobile communication device 510 configured to communicate with external defibrillator 108 through a local commlink 571. In some embodiments, mobile communication device 510 and local commlink 571 may be implemented as described in U.S. patent application Ser. No. 13/959,894 filed Aug. 6, 2013, and entitled "MOBILE COMMUNICATION DEVICE & APP FOR WEARABLE DEFIBRILLATOR SYSTEM". In embodiments, mobile communication device 510 can be a wireless telephone, a smartphone, a Personal Digital Assistant (PDA), a personal electronic device, a pager, a laptop computer, a tablet, an e-reader, and so on. Such mobile communication devices are increasingly becoming more than just wireless voice communication devices. In addition to handling voice data, many mobile communication devices are essentially portable computing devices that can support a variety of applications such as email, instant messaging, web browsing, text processing applications, contact applications, scheduling applications, games, and so on.

In other embodiments, the functionality of mobile communication device 510 may be incorporated directly into the external defibrillator 108. In such a case, no local comlink 571 is necessary as any communication between the functionality of the external defibrillator 108 and the functionality described in conjunction with the mobile communication device 510 would occur intra-device without need for an external communication channel. Mobile communication device 510 is illustrated and described as a separate component for clarity and completeness of discussion only.

In many cases, mobile communication device 510 acts as a proxy for the patient 182. Patient 182 may carry device 510 in a pocket, in a special holder, attached to a garment, on the patient's wrist or belt, or the like. In other words, the location of patient 182 can sometimes be presumed to be the same as the location of mobile communication device 510. In such embodiments, mobile communication device 510 includes a location module that has location determining circuitry and/or software for determining the location of the mobile communication device using, for example, GPS, Wi-Fi Positioning System (WPS), cell tower locations, Wi-Fi access point locations, inertial navigation, etc., as may be available in various smartphones.

The arrangement of FIG. 5 typically uses one or more wireless communication links. A communication link is also sometimes referred to herein as a "comlink". For purposes of this document, a "remote comlink" means a communication link established between devices that are typically about 500 feet (150 m) or more away from each other, and often farther, such as a cellular communication link. A "local comlink" as used in this context means a communication link established directly between devices that are less than about 500 feet (150 m) away from each other, and typically much closer. A commlink may be either wireless, wired, or some combination of wireless and wired communication links.

In accordance with the disclosure, a "local area" 501 refers to a proximate location around the patient 182. In some embodiments, the local area 501 may be defined by the effective communication distance between the patient 182 (or the patient's device 510) and other devices (e.g., responder device 591). For example, the local area 501 may be defined by the effective communication distance. In other embodiments, the local area 501 may be defined by a certain distance (e.g., 50 feet, 100 feet, or the like) around the patient 182. In still other embodiments, the local area 501 may be defined by (or influenced by) a radius of accuracy of GPS equipment employed by either the patient's device 510 or other communication equipment, such as responder devices (e.g., responder devices 591-593).

In embodiments, mobile communication device 510 can communicate with a wireless service provider network 580 via a remote comlink 572. Remote comlink 572 can be direct, or can be established between device 510 and network 580 via intermediary points, such as a Wireless Access Point, Wi-Fi, and so on; even in those cases, however, a remote comlink includes at least one leg of communication link that is at least 500 feet (150 m) long. One or more of the legs between intermediary points may include a network land line. Network 580 can be coupled with a communications network 480, which can be any wide area network, such as the Internet, POTS, etc. Receiving devices 490 of the responders can be part of network 480, and in effect be cloud-based. Receiving devices 490, in embodiments, may be any one of a landline telephone, a cellular telephone, a desktop computer, a server, a mainframe computer, and so on. Accordingly, mobile communication device 510 can communicate and exchange data directly or indirectly with receiving devices 490 of remote responders, at least according to the arrangement of FIG. 5.

In some embodiments, a WCD server 585 processes notification information received via communication network 480 to generate one or more notification messages. For example, in some embodiments, WCD server 585 is configured with profile and preference information for each responder and generates the appropriate notification message for that responder (and/or the responder's device 590). For receiving devices 590 that are wireless (e.g., cell phones, smartphones, connected tablets, connected laptops, pagers, etc.), WCD system server 585 in some embodiments generates one or more SMS messages, recorded/synthesized voice messages, emails, or the like to be sent to those devices via a wireless service provider network 480 and a remote comlink 572. Similarly, for receiving devices 590 that are wired or potentially wired (e.g., a landline telephone, a desktop computer, etc.), WCD system server 585 in some embodiments generates one or more email messages, recorded or synthesized voice messages, or the like to be sent to those devices via a wired comlink 572 such as the Internet, POTS, etc. The particular type of notification message for each receiving device 590 may be selected by WCD system server 585 based on contact information, emergency event and/or stored profile/preference information.

In some embodiments, mobile communication device 510 and/or receiving devices 490 includes an application, also known as an "app" that facilitate the users of these devices in sending and receiving communications, including notifications.

In many embodiments, external defibrillator 108 and mobile communication device 510 are capable of establishing local comlink 571, and therefore can exchange data between them via the local comlink. Data can be exchanged in either direction, or in both directions. In some embodiments, local comlink 571 uses radio transmission technology that can be broadband and/or shortwave. Local comlink 571 may use Bluetooth technology, Wi-Fi technology, Near Field Communication, or other wireless technology. Local comlink 571, coupled with the abilities of mobile communication device 510, enables external defibrillator 108 to communicate better with its environment.

In other embodiments, instead of wireless comlink 571, defibrillator 108 and mobile communication device 510 may be capable of establishing a comlink that is wired, and therefore can exchange data between them via the wired local comlink. The wired comlink can be by any suitable wired connection, for example via a USB or Lightning connection. Communication could be established by the connecting, whereupon the two devices would recognize each other, and so on.

For example, to send a notification, external defibrillator 108 may use local comlink 571 to provide emergency event information to mobile communication device 510. In some embodiments, external defibrillator 108 also provides patient location information and/or patient ID information to mobile communication device 510. In some embodiments, external defibrillator 108 may be configured to send the emergency event information to mobile communication device 510 before or concurrently with the determination that notifications should be sent to responder(s).

Mobile communication device 510 then uses remote link 572 to provide information related to the emergency event, patient ID, and location (Notification 573) to wireless service provider network 580. Mobile communication device 510 typically uses responder contact information stored in its memory to direct information to responder devices (e.g., responders 591-593). In other embodiments, mobile communication device 510 obtains the contact information form external defibrillator 108. In some embodiments, mobile communication device 510 is configured with the patient ID information, and can obtain the location information using its own location determination functionality (as opposed to obtaining it from external defibrillator 108). In some embodiments, the Notification 573 includes information processed and/or revised from the event information obtained from external defibrillator 108 to comply with patient privacy regulations and to provide only what is needed by potential responders to be able to quickly travel to the patient and provided assistance such as, for example, CPR.

Wireless service provider network 580, in some embodiments, then uses communication network 480 to provide Notification 573 to the responder device(s) 590. However, in embodiments of the present disclosure, the notifications to responder device(s) can be disabled (or not sent) based on the whether the responder device(s) 590 are near the patient 182 (e.g., within local area 501). In other words, when Notification 573 is transmitted, various responders (591, 592, 593) may be geographically distributed. Some responders (e.g., responders 592-593) may be geographically distant from the patient 182 while other responders (e.g., responder 591) may be within local area 501.

In some embodiments, the proximity of a potential responder can be determined by a WCD system server 585 tracking the locations of the patient 182 (via the WCD system or the patient's device 510) and any potential responders' communication devices 590. For example, the WCD system server may periodically send a request to each of the responders' communication devices for its location (which typically include location determination technology). In other embodiments, each of the responders' communication devices is loaded with an app that is configured to periodically send its location to the WCD system server 585. In other embodiments, the WCD system may determine proximity of a responder's device (e.g., responder 591) using the local discovery function (574) available in mobile devices, such as Bluetooth, Wi-Fi direct, or NFC communications.

In some embodiments, when an event occurs that would cause the WCD system to alert potential responders, the WCD system server 585 may be configured to only send the alert to responder devices that are outside the local area 501. For example, the local area 501 may be a preselected distance such as, for example, 10 ft., or it can be dynamically determined by the alert settings on the WCD itself (e.g., if the audio alerts have been set to a relatively low level, the threshold may be dynamically set to a shorter distance such as 5 ft.).

In some embodiments, instead of not sending an alert to the "nearby" responders (e.g., responder 591), the WCD system server 585 may send a simple alert such as "Assist Patient" to the responder's device that automatically terminates without that responder having to perform any operations on his/her device.

In other embodiments, rather than not sending a notification to the "nearby" responders (e.g., responder 591), each responder device 590 may alternatively be configured to silence or mute any notification received when the responder is within the local area 501. In yet other embodiments, notifications received by the responder devices 590 may include information that indicates whether the notification is "urgent" and should be announced even though the responder is within the local area 501.

In some embodiments, the WCD system continues to track the location of the "nearby" responder device(s) that did not receive an alert (e.g., responder 591). If such a device moves away from the patient 182 or remains in the same location for a certain time period (e.g., 20 seconds), the WCD system server 585 may issue an alert to that responder's device in case the responder did not hear the patient's alert. In some embodiments, if the nearby responder's location is adjacent to the patient, the WCD system server 585 may be configured to not send an alert if the nearby responder 591 remains in the same location, or detects that the nearby responder 591 is performing assistance activity (e.g., calling 911), or receives data from the patient's device 510 that CPR is being performed on the patient (e.g., from accelerometer and/or transthoracic impedance signals).

In other embodiments, the WCD system continues to track the location of the "far" responder device(s) (e.g., responders 592, 593) that did receive an alert. If none of these "far" responder device(s) move nearer to the patient within a certain time period (e.g., 20 seconds), the WCD system server 585 may be configured to resend the alert(s) to those "far" responder device(s) that did not move nearer to the patient. In some embodiments the WCD system server may be configured to not resend the alert to such "far" responders if it detects that other responders (including "nearby" responder 591) are performing assistance activity for the patient 182.

Embodiments can be advantageous in many instances, such as when the responder 591 is a layperson not used to providing assistance in an emergency situation. An alert notification sent to the responder 591 while providing assistance could confuse the responder 591 or cause the responder 591 to interrupt assistance in order to determine what the alert received on the responder's device is. By not sending or muting an alert to the nearby responder 591 (who should be able to hear the alert from the patient's device 510), the nearby responder 591 is spared from having to deal with distracting and potentially confusing alerts received on his/her device and thereby be more likely to quickly provide the needed assistance.

In other embodiments, in addition to messaging that are triggered by events at the patient's WCD, the WCD system can control any messaging to the responder based on the proximity of the responder to the patient's WCD. For example, the WCD system may detect when a responder is near the patient and send a message to that responder to encourage the patient to engage in some desired activity (e.g., to walk, drink water, relax, etc.) or stop engaging in an undesirably activity (e.g., overexertion if heart rate is too high, driving or standing if patient is experiencing bradycardia, etc.).

In yet other embodiments, the nearby responder 591 may activate a local notification condition by "tapping" the local responder's device to the patient's device 510 or a component of the WCD (e.g., defibrillator 108). It will be appreciated that "tapping," as used herein, means a wireless communication between two electronic components by bringing the two components in close proximity to each other. As used herein, "tapping" includes a physical touching but also includes merely bringing two components near enough to each other to initiate a wireless communication, such as an NFC communication, which may be contactless. In this way, a nearby responder, such as a more sophisticated responder (e.g., EMT personnel), may be able to override any automatic muting of notifications in order to ensure that all notifications are received even locally.

The various embodiments of the devices and/or systems disclosed in this document perform functions, processes and/or methods as described above. These functions, processes and/or methods may be implemented by one or more devices that include logic circuitry. Such a device can be alternately called a computer, and so on. It may be a standalone device or computer, such as a general-purpose computer, or part of a device that has one or more additional functions. In some embodiments, the computer is a specialized computer adapted to and optimally configured for a specific purpose such as for example, providing therapy shocks in emergency situations. The logic circuitry may include a processor and non-transitory computer-readable storage media, such as memories, of the type described in this document. Often, for the sake of convenience, it is preferred to implement and describe a program as various interconnected distinct software modules or features. These, along with data are individually and also collectively referred to herein as software. In some instances, software is combined with hardware, in a mix called firmware.

Various embodiments of methods and algorithms are described below. These methods and algorithms are not necessarily inherently associated with any particular logic device or other apparatus. Rather, they can be advantageously implemented by programs for use by a computing machine, such as a general-purpose computer, a special purpose computer, a microprocessor, a microcontroller, a processor and/or a combination of these devices such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts describe methods in terms of boxes, they also concurrently describe programs.

Figure 6:
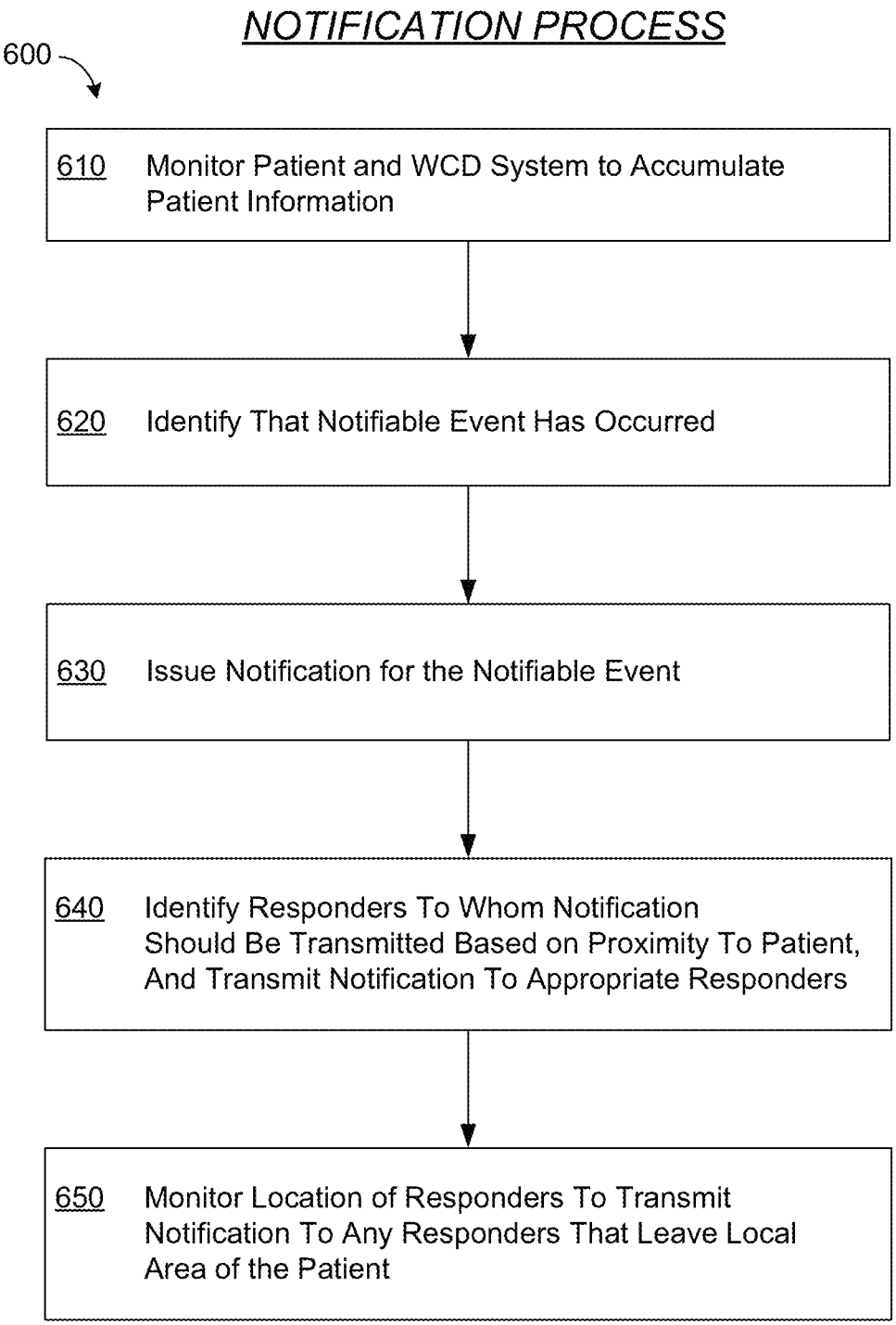
FIG. 6 is a flow diagram illustrating sample methods for use in a WCD system to notify remote responders, according to embodiments.

FIG. 6 is a flow diagram generally illustrating a notification process 600 for use in a WCD system (such as described above in conjunction with FIGS. 2-5) to notify remote responders of a notifiable event, according to embodiments. Notification process 600, in some embodiments, can start when the WCD system encounters a notifiable event as previously described.

At operation 610, the process 600 monitors a patient, the WCD system itself, and perhaps environmental conditions to accumulate patient information. The patient information may include patient state parameters, system parameters, environmental parameters, and the like.

At operation 620, the process 600 identifies that a notifiable event has occurred. The notifiable event may be any occurrence deemed, by the WCD system programming, to warrant issuing a notification to systems or individuals external to the WCD system. Non-exhaustive examples of notifiable events include medical events pertaining to the health of the patient (e.g., arrythmia, SCA, or the like), events pertaining to the patient's compliance with prescribed wear of the WCD system, maintenance events (e.g., low battery warnings, electrode expiry, other system warnings or the like), manually entered event notifications (e.g., weartime compliance indicators, geofencing indicators, etc.), and any other occurrence detectable by the WCD system. It should be noted that all "events" detectable by the WCD system need not necessarily constitute a "notifiable event" within the context of this disclosure (although they could).

At operation 630, the process 600 issues a notification for the notifiable event. For the purpose of this disclosure, the term "notification" means a message that includes information about the patient, the WCD system, the environment, or any other fact or circumstance the notice of may be beneficial to a responder rendering aid to the patient. As used in this disclosure, an "alert" is a specific type of "notification." Issuing the notification at operation 630 may include transmitting the notification to a WCD system server for dissemination to one or more responders.

At operation 640, the process 600 identifies responders to whom the notification issued at operation 630 should be transmitted. As describe at length above, different responders may be in disparate geographic locations with respect to the patient. In this particular embodiment, the process 600 identifies any responder that is within a local area of the patient. Based on such determination, the process 600 transmits the notification to any responders that are not within the local area, and does not transmit the notification to any responders that are within the local area.

At operation 650, the process 600 continues to monitor the location of any responders identified as within the local area of the patient in operation 640. If and when any such responder leaves the local area of the patient, the process 600 may transmit any notifications that had not been previously transmitted to such responder upon determining that such responder is no longer in the local area of the patient. In many cases, notifications may be time sensitive or time dependent. In such cases, notifications that are no longer relevant or important may be omitted.

Figure 7:
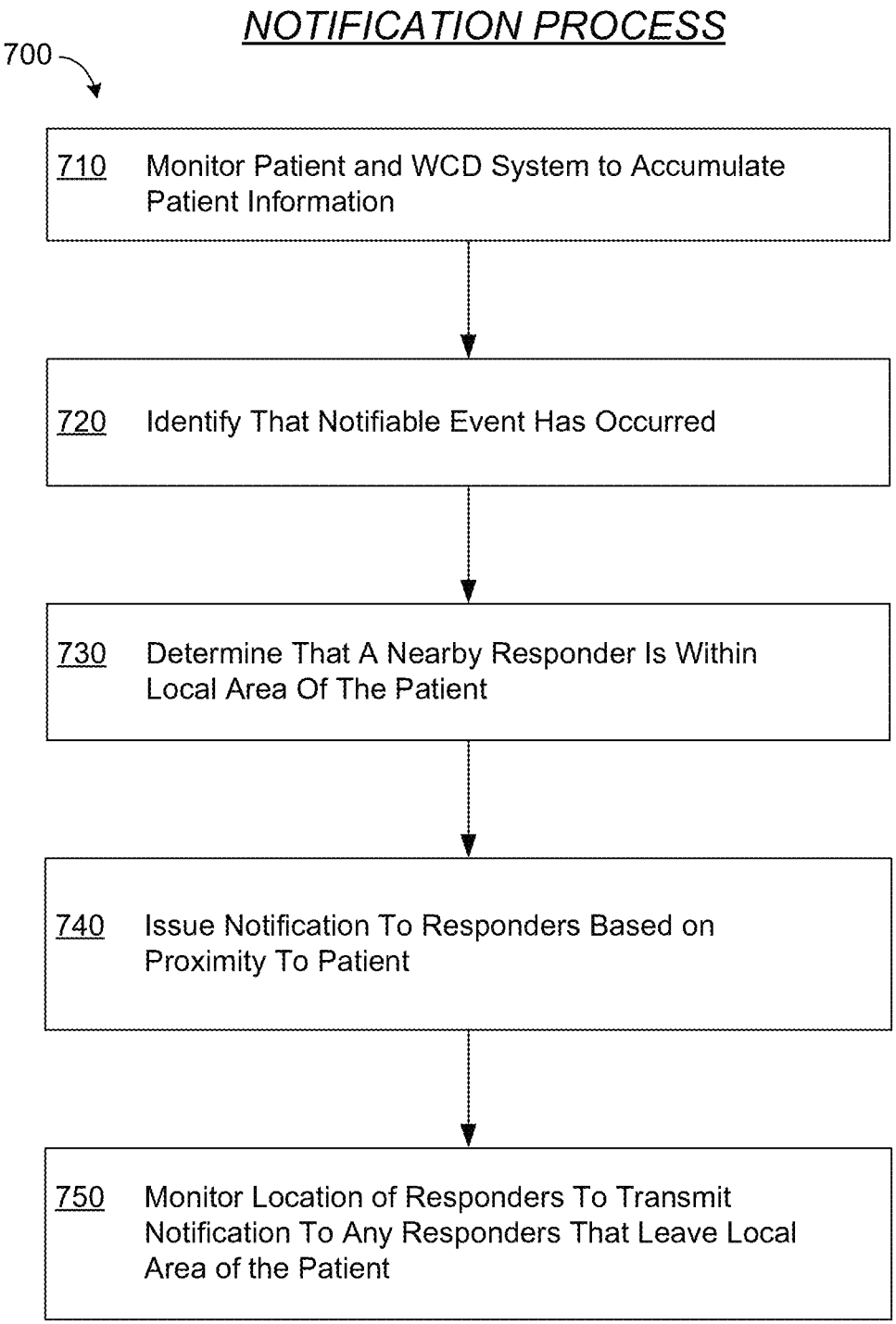
FIG. 7 is another flow diagram illustrating sample methods for use in a WCD system to notify remote responders, according to embodiments.

FIG. 7 is another flow diagram generally illustrating a notification process 700 for use in a WCD system (such as described above in conjunction with FIGS. 2-5) to notify remote responders of a notifiable event, according to embodiments. Notification process 700, in some embodiments, can start when the WCD system encounters a notifiable event as previously described.

At operation 710, the process 700 monitors a patient, the WCD system itself, and perhaps environmental conditions to accumulate patient information. The patient information may include patient state parameters, system parameters, environmental parameters, and the like.

At operation 720, the process 700 identifies that a notifiable event has occurred. The notifiable event may be any occurrence deemed, by the WCD system programming, to warrant issuing a notification to systems or individuals external to the WCD system. Non-exhaustive examples of notifiable events include medical events pertaining to the health of the patient (e.g., arrythmia, SCA, or the like), events pertaining to the patient's compliance with prescribed wear of the WCD system, maintenance events (e.g., low battery warnings, electrode expiry, other system warnings or the like), manually entered event notifications (e.g., wear-time compliance indicators, geofencing indicators, etc.), and any other occurrence detectable by the WCD system. It should be noted that all "events" detectable by the WCD system need not necessarily constitute a "notifiable event" within the context of this disclosure (although they could).

At operation 730, the process 700 determines that a responder is within a local area of the patient (a "nearby responder"). The process 700 may make such determination by, for example, receiving a communication from the responder that includes location information of the responder. Such communication may be received either directly or indirectly from the nearby responder. For instance, the communication may take the form of a GPS location transmitted, either directly or indirectly, from the nearby responder to the WCD system. Alternatively, the process 700 may make such determination by determining that the nearby responder has engaged with the WCD system such as, for example, by "tapping" a mobile device with an NFC facility to the WCD system, by making a Wi-Fi direct connection to the WCD system, or by making a Bluetooth pairing with the system.

It should be noted that, in accordance with process 700, operation 720 and operation 730 do not necessarily occur in serial order and may occur simultaneously. In addition, either operation may occur prior to or after the other.

At operation 740, the process 700 issues a notification for the notifiable event. For the purpose of this disclosure, the term "notification" means a message that includes information about the patient, the WCD system, the environment, or any other fact or circumstance the notice of may be beneficial to a responder rendering aid to the patient. As used in this disclosure, an "alert" is a specific type of "notification." Issuing the notification at operation 740 may include transmitting the notification to a WCD system server for dissemination to one or more responders. In accordance with the process 700, the notification issued at operation 740 is transmitted only to responders other than the nearby responder. Alternatively, the nearby responder may be configured to silence or mute the notification while within the local area of the patient.

At operation 750, the process 700 continues to monitor the location of the nearby responder identified at operation 730. If and when the nearby responder leaves the local area of the patient, the process 700 may transmit any notifications that had not been previously transmitted to such responder upon determining that such responder is no longer in the local area of the patient. In many cases, notifications may be time sensitive or time dependent. In such cases, notifications that are no longer relevant or important may be omitted.

In various implementations, the notifications may take any one or more of various forms. For instance, notifications may take the form of pre-recording audible messages. Alternatively, notifications may take the form of electronic messages assembled using the appropriate patient information and delivered via electronic means. In yet another alternative, notifications may be transmitted using a cellular SMS system. In still another alternative, notifications may be transmitted as electronic communications between a host and client each operating special purpose programmed applications. In various combinations and implementations, combinations of one or more of the foregoing protocols may be employed, even in combination with other communication protocols.

In the methods described above, each operation can be performed as an affirmative step of doing, or causing to happen, what is written that can take place. Such doing or causing to happen can be by the entire system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily the present invention. Plus, any reference to any prior art in this description is not, and should not be taken as, an acknowledgement or any form of suggestion that this prior art forms parts of the common general knowledge in any country.

This description includes one or more examples, but that does not limit how the invention may be practiced. Indeed, examples or embodiments of the invention may be practiced according to what is described, or yet differently, and also in conjunction with other present or future technologies. Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, a phrase in the form of "A and/or B" is used to indicate "A or B or both A and B". Further, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in any number of ways, as will be apparent to a person skilled in the art after reviewing the present disclosure, beyond any examples shown in this document.

The following claims define certain combinations and subcombinations of elements, features and steps or operations, which are regarded as novel and non-obvious. Additional claims for other such combinations and subcombinations may be presented in this or a related document.

What is claimed is:

1. A wearable cardioverter defibrillator (WCD) system, comprising:
    a support structure configured to be worn by a patient;
    a plurality of electrodes coupled to or integrated in the support structure;
    an energy storage module configured to store an electrical charge;
    a discharge circuit configured to be coupled to the energy storage module and configured to deliver one or more shocks to the patient while the support structure is worn by the patient using the plurality of electrodes and the electrical charge stored in the energy storage module;
    a location module configured to determine a WCD location, the WCD location being a location of a component of the WCD system;
    an event detection module configured to detect an occurrence of a notifiable event;
    a notification module coupled to the event detection module, the notification module being configured to generate a notification of the notifiable event;
    a communication module, coupled to the notification module, configured to transmit the notification, wherein the notification is configured to cause a responder notification to be communicated to a responder device in response to a determination that the responder device is outside a local area of the WCD location; and
    a WCD system server configured to:
        receive the notification and the WCD location from the communication module;
        acquire a location of the responder device;
        compare the WCD location to the location of the responder device;
        determine whether the responder device is within the local area of the WCD location;
        transmit the responder notification to the responder device responsive to a determination that the location of the responder device is outside of the local area of the WCD location;
        determine whether the responder device moves closer to the WCD location within a time period; and
        when the responder device does not move closer to the WCD location within the time period, issue a second alert to the responder device.

2. The WCD system of claim 1, wherein the WCD system server is further configured to:
    determine whether the responder device is adjacent to the WCD location; and
    when the responder device is adjacent to the WCD location, not issue the second alert to the responder device.

3. The WCD system of claim 1, further comprising a mobile communication device configured to implement at least a part of the communication module.

4. The WCD system of claim 3, wherein the mobile communication device further implements the location module.

5. The WCD system of claim 1, wherein the communication module is (Original) further configured to not transmit the responder notification to the responder device when the responder device is within the local area of the WCD location.

6. The WCD system of claim 1, wherein the communication module is further configured to transmit the responder notification to the responder device when the responder device further is within the local area of the WCD location, and wherein the responder device is further configured to silence the notification when the responder device is within the local area of the WCD system.

7. The WCD system of claim 6, wherein the communication module is configured to transmit the notification of the notifiable event to the WCD system server, and wherein the WCD system server determines whether the responder device is within the local area of the WCD location and, if so, the WCD system server is configured to not transmit the responder notification to the responder device.

8. The WCD system of claim 1, wherein the local area of the WCD location is defined by an effective communication distance of the communication module using a local communication facility.

9. The WCD system of claim 1, wherein the local area of the WCD location is defined by a specified distance from the component of the WCD system.

10. The WCD system of claim 1, wherein the local area of the WCD location is determined by an engagement of the WCD system by the responder device.

11. The WCD system of claim 10, wherein the engagement of the WCD system comprises a Bluetooth pairing between the WCD system and the responder device.

12. The WCD system of claim 10, wherein the engagement of the WCD system comprises tapping the responder device to the WCD system in accordance with a Near Field Communication facility.

13. A method for use in a wearable cardioverter defibrillator (WCD) system comprising a support structure configured to be worn by a patient, and a plurality of electrodes coupled to or integrated in the support structure, the method comprising:
    monitoring, by the WCD system one or more parameters of the patient of the WCD system, or of both the patient and the WCD system;
    determining, by the WCD system, a location of the patient;
    determining, by the WCD system, that a notifiable event has occurred, the notifiable event implicating at least one of the one or more parameters;
    responsive to a determination by the WCD system that the notifiable event has occurred, generating a notification of the notifiable event;
    initiating, by the WCD system, transmission of a responder notification to a responder device that is outside a local area of the location of the patient in response to the generation of the notification and a determination that the responder device is outside the local area of the patient;

acquiring a location of the responder device with a WCD server;

comparing a WCD location to the location of the responder device;

determining whether the responder device moves closer to the WCD location within a time period; and when the responder device does not move closer to the WCD location within the time period, issuing a second alert to the responder device.

14. The method of claim 13, wherein the WCD further comprises a mobile communication device, wherein the mobile communication device is used, at least in part, in determining the location of the patient, and wherein the mobile communication device assists with the transmission of the responder notification.

15. The method recited in claim 13, wherein the one or more parameters comprise one or more physiological parameters of the patient while the patient is wearing the support structure, and one or more system parameters of the WCD system that reflect a status of the WCD system.

16. The method of claim 13, further comprising disregarding transmission of the responder notification to another responder device that is within the local area of the location of the patient.

17. The method of claim 16, further comprising reinitiating transmission of the responder notification to the another responder device when the another responder device is outside the local area of the location of the patient.

18. The method of claim 13, wherein the notifiable event comprises at least one of a medical event associated with the patient or a maintenance event associated with the WCD system.

19. The method of claim 13, wherein the local area of the patient is defined by either an effective communication distance of the WCD system using a local communication facility, or a specified distance from the WCD system.

20. The WCD system of claim 1, wherein the responder notification comprises at least part of the notification.

* * * * *